United States Patent [19]

Kubo et al.

[11] Patent Number: 5,685,356
[45] Date of Patent: Nov. 11, 1997

[54] METHOD OF MAKING DENTAL WAX PATTERN

[75] Inventors: Fuminobu Kubo, Katano; Kazuhiko Joshin, Yokosuka, both of Japan

[73] Assignee: GC Corporation, Tokyo, Japan

[21] Appl. No.: 495,394

[22] Filed: Jun. 28, 1995

[30] Foreign Application Priority Data

Jul. 12, 1994 [JP] Japan .................. 6-184080

[51] Int. Cl.$^6$ ................................. B22C 7/02
[52] U.S. Cl. ................................ 164/45; 164/35
[58] Field of Search .................. 164/45, 35, 517, 164/235

[56] References Cited

U.S. PATENT DOCUMENTS

| | | | |
|---|---|---|---|
| 3,747,663 | 7/1973 | Taylor | 164/45 |
| 4,745,961 | 5/1988 | Salandra | 164/45 |

FOREIGN PATENT DOCUMENTS

| | | | |
|---|---|---|---|
| 59-78748 | 5/1984 | Japan | 164/45 |
| 60-92338 | 5/1985 | Japan | 164/45 |
| 61-37348 | 2/1986 | Japan | 164/45 |
| 1025478 | 6/1983 | U.S.S.R. | 164/517 |

Primary Examiner—Joseph J. Hail, III
Assistant Examiner—I.-H. Lin
Attorney, Agent, or Firm—Oblon, Spivak, McClelland, Maier & Neustadt, P.C.

[57] ABSTRACT

A method of making a wax pattern by using a dental gypsum model is provided, which comprises the steps of applying a release agent on said gypsum model, coating on the thus applied surface a coating material which leaves no ash upon incinerated at 700° C., and applying a wax melt on said surface. When the wax melt is applied on the gypsum model, the wax is in no direct contact with the release agent, and it is unlikely that gaps may be formed between the wax pattern and the gypsum model or a pad of the wax pattern may warp; that is, the additional operation so far needed for correcting such warpage can be dispensed with, so making precise casting possible. In addition, the presence of the release agent enables removal of the wax pattern to be done as conventional. Furthermore, when the thus removed wax pattern is invested in a investment material to incinerate the wax pattern, no ash of the above coating material remains in the cavity, so that metal can be cast with no defect.

5 Claims, No Drawings

METHOD OF MAKING DENTAL WAX PATTERN

BACKGROUND OF THE INVENTION

1. Field of the Invention

The present invention relates to a method of making a wax pattern for crowns or inlays by using a dental gypsum model.

2. Prior Art

When a dental gypsum model is used to make a wax pattern for crowns or inlays, for instance, when a wax melt is applied on a gypsum model for crown making to make a wax pattern of the same shape as a crown's, a curing agent such as polyethylene resin is applied on the gypsum model to cure the gypsum model for reinforcing purposes. Then, a release agent for facilitating release of the wax pattern, for instance, silicone oil is applied on the applied surface. Finally, a wax melt is coated on the thus applied surface to form a crown pattern.

However, since the wax melt is directly coated on the surface with the release agent applied on it, an opening or marginal portion of the wax pattern formed by the cooling and solidification of the wax melt warps due to the repulsion force between the wax pattern and the gypsum model. In addition, gaps are likely to be formed between them. Such warpage must be corrected as by use of a heated graver or metal spatula to fill the above gaps.

An object of the present invention is to prevent or inhibit any warpage of wax by preventing direct contact of a wax melt with the surface with the release agent coated on it.

SUMMARY OF THE INVENTION

According to the present invention, the above-described object is achieved by the provision of a method of making a wax pattern by using a dental gypsum model, which comprises the steps of applying a release agent on said gypsum model, coating on the thus applied surface a coating material which leaves no ash upon incineration at 700° C., and applying a wax melt on said surface.

The coating material used herein may be of either an aqueous type or an emulsion type, provided that no ash remains after the wax pattern is incinerated at 700° C. However, it is preferable to use an emulsion type of coating material such as acrylic emulsion, polyurethane emulsion or epoxy emulsion, among which the acrylic emulsion is preferred because it provides a film of excellent strength and is easy to handle. It is here to be noted that the emulsion type of coating material has preferably a solid content of 35 to 60%.

The above emulsion type of coating material may be used alone or in combination with a wax emulsion. In the latter case, the adhesion of the coating material to the wax pattern is improved. Preferably, the amount of the wax emulsion used is 20 to 80% of the total amount of it and the emulsion type of coating material.

The above coating material is coated on the gypsum model after the release agent applied thereon is dried up. The thickness of the coated layer after dried is preferably 0.01 to 0.1 mm. It is here to be noted that prior to application of the release agent, a curing agent may be applied on the gypsum model as has been done.

In the present invention, a tough film of the coating material is formed on the inner part of the wax pattern while the wax is in no direct contact with the release agent applied on the gypsum model. It is unlikely that gaps may be formed between the gypsum model and the wax pattern or a part of the wax pattern may warp. Thus, the wax pattern can be formed with an improved precision. The wax pattern of desired shape is formed on the gypsum model. Upon cooled, the wax pattern is then released from the gypsum model. In this case, since the release agent has been applied on the surface of the gypsum model, an easy release of the wax pattern from the gypsum model is achieved. By this release, the coating material is transferred from the gypsum model to the wax pattern Then, this material is invested in an investment material together with the wax pattern, whereupon the wax pattern is incinerated out at 700° C. Since no ash of the coating material remains in the cavity in the investment, a casting of good quality is obtained by metal casting owing to the absence of defects such as surface roughness and pores.

When the coating material used is of the emulsion type, esp., the acrylic emulsion type, the warpage of the wax pattern is significantly reduced owing to an increased coating film strength. When a wax emulsion is added to the above coating material, the adhesion of the coating to the wax model is remarkably improved. However, the wax emulsion, when used in an amount of 20% or less based on the total amount, is ineffective, and when used in an amount of 80% or more, provides a coating film with poor strength. The resulting coating film is less than satisfactory at a thickness of 0.01 mm or less, and is likely to peel off the wax pattern at a thickness exceeding 0.1 mm.

EXAMPLE

The present invention will now be explained with reference to some examples by way of illustration alone but not by way of limitation.

Example 1

In forming a crown form of wax pattern on a dental crown-making gypsum model, a solution of polystyrene resin was applied on the gypsum model as a curing agent, followed by the application of a silicone oil serving as a release agent. A coating material or an acrylic emulsion ("JSR Acrylic Emulsion AE951 (F)" made by Nippon Gosei Rubber Co., Ltd. and having a solid content of 52%) was then coated on the dried surface of the silicone oil to obtain a coating film having a thickness of 0.02 mm as measured after drying. Then, a wax melt was applied on the coating film to form a crown. The obtained crown did not warp at the opening, and formed no gap with respect to the gypsum model. In addition, the crown form of wax pattern was easily released from the gypsum model.

Subsequently, the thus released crown form of wax pattern was invested in a phosphate type of investment material, which was then heated to 700° C. to incinerate out the wax pattern. A gold alloy melt was cast into the resultant cavity for crown casting. The resulting elaborate gold alloy crown had no foreign matter deposited on its surface, and was much the same shape as the wax pattern's.

Examples 2–4

Examples 2–4 were carried out following Example 1 with the exception that a wax emulsion ("Cellosol 967" made by Chukyo Yushi Co., Ltd. and having a wax content of 59%) was added to the above acrylic emulsion (coating material) at the proportion of 25/75, 50/50, and 75/25, thereby obtaining wax patterns. The results were similar to those of Example 1.

Example 5

This example was carried out following Example 1 with the exception that instead of the above acrylic emulsion an aqueous emulsion of styrene acrylate ester ("Movinyl DM 60" made by Hext Gosei Co., Ltd. and having a solid content of 50%) was used as the coating material, thereby obtaining a wax pattern. The results were similar to those of Example 1.

Example 6

This example was carried out following Example 5 with the exception that a wax emulsion ("Cellosol 524" made by Chukyo Yushi Co., Ltd. and having a wax content of 30%) was added to the above coating material at the proportion of 50/50, thereby obtaining a wax pattern. The results were similar to those of Example 5.

Example 7

This example was carried out following Example 1 with the exception that instead of the above acrylic emulsion an urethane lacquer ("Olester NL2249E" made by Mitusi Toatsu Chemicals Inc.) was used as the coating material, thereby obtaining a wax pattern. The results were similar to those of Example 1.

As recited in claim 1, the present invention provides a method of making a wax pattern by using a dental gypsum model, which comprises the steps of applying a release agent on said gypsum model, coating on the thus applied surface a coating material which leaves no ash, upon incinerated at 700° C., and applying a wax melt on said surface. According to this method, when the wax melt is applied on the gypsum model, the wax is in no direct contact with the release agent. It is unlikely that gaps may be formed between the wax pattern and the gypsum model or a part of the wax pattern may warp; that is, the additional operation so far needed for correcting such warpage can be dispensed with, so making precise casting possible. In addition, the presence of the release agent enables removal of the wax pattern to be done as conventional. Furthermore, when the thus removed wax pattern is invested in a investment material to incinerate out the wax pattern, no ash of the above coating material remains in the cavity, so that metal can be cast with no defect.

As recited in claim 2, an emulsion type of coating material selected from acrylic emulsion, polyurethane emulsion and epoxy emulsion is used as the coating material. This coating material provides a coating film of excellent strength and is easy to handle.

As recited in claim 3, a wax emulsion is added to the above emulsion type of coating material. This enables the adhesion of the coating film to the wax pattern to be so improved that the coating material cannot peel off the wax pattern.

What is claimed is:

1. A method of making a dental wax pattern, comprising:
   applying a coating of a release agent onto the surface of a dental gypsum model;
   coating the release agent coated model with an emulsified polymer coating material selected from the group consisting of an acrylic emulsion, a polyurethane emulsion and an epoxy emulsion, which does not leave an ash residue upon incineration at 700° C.; and then
   applying a molten wax onto said coated model surface.

2. The method of claim 1, wherein the thickness of the coated model surface prior to application of wax ranges from 0.01 mm to 0.1 mm.

3. The method of claim 1, wherein a wax emulsion is combined with said polymer coating emulsion in an amount of 20 to 80% of the total coating emulsion.

4. The method of claim 1, wherein the emulsified polymer coating material has a solids content of 35 to 60%.

5. The method of claim 1, wherein prior to coating said gypsum model with a release agent, the model is coated with a curing agent.

* * * * *